(12) United States Patent
Kwok et al.

(10) Patent No.: US 8,813,748 B2
(45) Date of Patent: *Aug. 26, 2014

(54) FULL-FACE MASK AND MASK CUSHION THEREFOR

(75) Inventors: Philip Rodney Kwok, Chatswood (AU); Robert Edward Styles, Glenhaven (AU); Gregory Scott Smart, Randwick (AU)

(73) Assignee: ResMed Limited, Bella Vista (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/293,684

(22) Filed: Nov. 10, 2011

(65) Prior Publication Data

US 2012/0090618 A1    Apr. 19, 2012

Related U.S. Application Data

(63) Continuation of application No. 11/432,436, filed on May 12, 2006, now Pat. No. 8,056,561, which is a continuation of application No. 10/704,754, filed on Nov. 12, 2003, now Pat. No. 7,069,933, which is a continuation of application No. 10/166,282, filed on Jun. 11, 2002, now Pat. No. 6,701,927, which is a continuation of application No. 09/316,227, filed on May 21, 1999, now Pat. No. 6,513,526, which is a continuation-in-part of application No. 08/791,212, filed on Jan. 31, 1997, now Pat. No. 6,112,746.

(30) Foreign Application Priority Data

Jul. 26, 1996 (AU) ........................................ PO1265

(51) Int. Cl.
*A62B 18/08* (2006.01)
*A62B 18/02* (2006.01)

(52) U.S. Cl.
USPC ............ 128/206.24; 128/206.21; 128/206.28; 128/207.13

(58) Field of Classification Search
USPC ............. 128/206.21, 206.23–206.24, 206.28, 128/207.11, 207.13
See application file for complete search history.

(56) References Cited

U.S. PATENT DOCUMENTS

| 781,516 A | 1/1905 | Guthrie |
| 812,706 A | 2/1906 | Warbasse |

(Continued)

FOREIGN PATENT DOCUMENTS

| AU | 64058/86 | 4/1987 |
| AU | 91/77110 B | 11/1991 |

(Continued)

OTHER PUBLICATIONS

Office Action for corresponding European Application No. 10183685.6, mailed Nov. 7, 2011.

(Continued)

*Primary Examiner* — Rachel Young
(74) *Attorney, Agent, or Firm* — Nixon & Vanderhye P.C.

(57) ABSTRACT

A full-face cushion comprises a frame and a membrane. The membrane has an aperture into which the wearer's nose is received. The membrane is spaced away from the frame. Respective notches receive the bridge of the wearer's nose. The wearer's nose and lips are received through the aperture into the chamber within the mask body. The seal forming portion thus contacts both the surface of the wearer's nose and a portion of the wearer's face in the region between the bottom lip and the chin, and around the sides and over the bridge of the nose.

9 Claims, 9 Drawing Sheets

(56) References Cited

U.S. PATENT DOCUMENTS

| | | |
|---|---|---|
| 902,961 A | 11/1908 | Goodnow |
| 1,000,706 A | 8/1911 | Barnum |
| 1,081,745 A | 12/1913 | Johnston et al. |
| 1,105,127 A | 7/1914 | Drager |
| 1,192,186 A | 7/1916 | Greene |
| 1,206,045 A | 11/1916 | Smith |
| 1,310,825 A | 7/1919 | Ganzer |
| 1,632,449 A | 6/1927 | McKesson |
| 1,653,572 A | 12/1927 | Jackson |
| 1,653,592 A | 12/1927 | Jackson |
| 1,710,160 A | 4/1929 | Rice |
| 1,926,027 A | 9/1933 | Biggs |
| 1,975,797 A | 10/1934 | Montuori |
| 2,123,253 A | 7/1938 | Catt |
| 2,133,699 A | 10/1938 | Heidbrink |
| 2,166,164 A | 7/1939 | Lehmberg |
| 2,248,477 A | 7/1941 | Lombard |
| 2,254,854 A | 9/1941 | O'Connell |
| 2,317,508 A | 4/1943 | Heidbrink |
| 2,371,965 A | 3/1945 | Lehmberg |
| 2,376,871 A | 5/1945 | Fink |
| 2,415,846 A | 2/1947 | Eugene |
| 2,438,058 A | 3/1948 | Kincheloe |
| 2,465,973 A | 3/1949 | Bulbulian |
| 2,578,621 A | 12/1951 | Yant |
| 2,625,155 A | 1/1953 | Engelder |
| 2,875,757 A | 1/1954 | Galleher, Jr. |
| 2,710,602 A | 6/1955 | Maybach |
| 2,931,356 A | 4/1960 | Schwarz |
| D188,084 S | 5/1960 | Garelick |
| 2,939,458 A | 6/1960 | Lundquist |
| 3,013,556 A | 12/1961 | Galleher |
| 3,044,464 A | 7/1962 | Gray |
| 3,182,659 A | 5/1965 | Blount et al. |
| 3,189,027 A | 6/1965 | Bartlett |
| 3,193,624 A | 7/1965 | Webb et al. |
| 3,227,159 A | 1/1966 | Borgia at al. |
| 3,238,942 A | 3/1966 | Holley |
| 3,315,674 A | 4/1967 | Bloom et al. |
| 3,330,273 A | 7/1967 | Bennett |
| 3,330,274 A | 7/1967 | Bennett |
| 3,362,420 A | 1/1968 | Blackburn et al. |
| 3,363,833 A | 1/1968 | Laerdal |
| 3,521,630 A | 7/1970 | Westberg et al. |
| 3,556,122 A | 1/1971 | Laerdal |
| 3,580,051 A | 5/1971 | Blevins |
| 3,680,555 A | 8/1972 | Warncke |
| 3,700,000 A | 10/1972 | Hesse et al. |
| 3,720,235 A | 3/1973 | Schrock |
| 3,725,953 A | 4/1973 | Johnson et al. |
| 3,796,216 A | 3/1974 | Schwarz |
| 3,799,164 A | 3/1974 | Rollins |
| D231,803 S | 6/1974 | Huddy |
| 4,015,598 A | 4/1977 | Brown |
| 4,077,404 A | 3/1978 | Elam |
| D250,131 S | 10/1978 | Lewis et al. |
| 4,167,185 A | 9/1979 | Lewis |
| 4,174,710 A | 11/1979 | Pampuch |
| 4,226,234 A | 10/1980 | Gunderson |
| 4,245,632 A | 1/1981 | Houston |
| D262,322 S | 12/1981 | Mizerak |
| 4,304,229 A | 12/1981 | Curtin |
| 4,305,387 A | 12/1981 | Reist-Kündig et al. |
| 4,328,797 A | 5/1982 | Rollins et al. |
| 4,347,205 A | 8/1982 | Stewart |
| 4,354,488 A | 10/1982 | Bartos |
| 4,402,316 A | 9/1983 | Gadberry |
| 4,412,537 A | 11/1983 | Tiger |
| 4,414,973 A | 11/1983 | Matheson et al. |
| 4,454,880 A | 6/1984 | Muto et al. |
| 4,467,799 A | 8/1984 | Steinberg |
| 4,522,639 A | 6/1985 | Ansite et al. |
| 4,558,710 A | 12/1985 | Eichler |
| 4,574,799 A | 3/1986 | Warncke |
| 4,616,647 A | 10/1986 | McCreadie |
| 4,622,964 A | 11/1986 | Flynn |
| 4,655,213 A | 4/1987 | Rapoport et al. |
| 4,658,763 A | 4/1987 | Gobien et al. |
| 4,665,570 A | 5/1987 | Davis |
| 4,671,271 A | 6/1987 | Bishop et al. |
| 4,677,975 A | 7/1987 | Edgar et al. |
| 4,677,977 A | 7/1987 | Wilcox |
| 4,699,092 A | 10/1987 | Ruf et al. |
| H397 H | 1/1988 | Stark |
| D293,613 S | 1/1988 | Wingler |
| 4,739,755 A | 4/1988 | White et al. |
| 4,770,169 A | 9/1988 | Schmoegner et al. |
| 4,774,941 A | 10/1988 | Cook |
| 4,782,832 A | 11/1988 | Trimble et al. |
| 4,794,921 A | 1/1989 | Lindkvist |
| 4,799,477 A | 1/1989 | Lewis |
| 4,803,981 A | 2/1989 | Vickery |
| 4,809,692 A | 3/1989 | Nowacki et al. |
| 4,811,730 A | 3/1989 | Milano |
| 4,819,629 A | 4/1989 | Jonson |
| 4,821,713 A | 4/1989 | Bauman |
| 4,841,953 A | 6/1989 | Dodrill |
| 4,848,334 A | 7/1989 | Bellm |
| 4,848,366 A | 7/1989 | Aita et al. |
| 4,889,079 A | 12/1989 | Takeda et al. |
| 4,907,584 A | 3/1990 | McGinnis |
| 4,910,806 A | 3/1990 | Baker et al. |
| 4,919,128 A | 4/1990 | Kopala et al. |
| 4,922,921 A | 5/1990 | Donoghue |
| 4,938,210 A | 7/1990 | Shene |
| 4,938,212 A | 7/1990 | Gnook et al. |
| 4,944,310 A | 7/1990 | Sullivan |
| D310,431 S | 9/1990 | Bellm |
| 4,971,051 A | 11/1990 | Toffolon |
| 4,986,269 A | 1/1991 | Hakkinen |
| 4,989,596 A | 2/1991 | Macris et al. |
| 4,989,599 A | 2/1991 | Carter |
| 5,003,633 A | 4/1991 | Itoh |
| 5,005,568 A | 4/1991 | Loescher et al. |
| 5,005,571 A | 4/1991 | Dietz |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,063,922 A | 11/1991 | Hakkinen |
| 5,065,756 A | 11/1991 | Rapoport |
| 5,069,205 A | 12/1991 | Urso |
| D323,908 S | 2/1992 | Hollister et al. |
| 5,094,193 A | 3/1992 | Yoshikawa |
| 5,109,839 A | 5/1992 | Blasdell et al. |
| 5,109,840 A | 5/1992 | Daleiden |
| 5,121,745 A | 6/1992 | Israel |
| 5,133,347 A | 7/1992 | Huennebeck |
| 5,140,980 A | 8/1992 | Haughey et al. |
| 5,140,982 A | 8/1992 | Bauman |
| 5,148,802 A | 9/1992 | Sanders et al. |
| 5,159,938 A | 11/1992 | Laughlin |
| 5,178,138 A | 1/1993 | Walstrom et al. |
| D334,633 S | 4/1993 | Rudolph |
| 5,220,699 A | 6/1993 | Farris |
| 5,231,983 A | 8/1993 | Matson et al. |
| 5,233,978 A | 8/1993 | Callaway |
| 5,243,971 A | 9/1993 | Sullivan et al. |
| 5,265,595 A | 11/1993 | Rudolph |
| 5,279,289 A | 1/1994 | Kirk |
| 5,280,784 A | 1/1994 | Kohler |
| 5,297,544 A | 3/1994 | May et al. |
| 5,311,862 A | 5/1994 | Blasdell et al. |
| 5,322,057 A | 6/1994 | Raabe et al. |
| 5,322,059 A | 6/1994 | Walther |
| 5,323,774 A | 6/1994 | Fehlauer |
| 5,343,878 A | 9/1994 | Scarberry et al. |
| 5,349,949 A | 9/1994 | Schegerin |
| 5,357,951 A | 10/1994 | Ratner |
| 5,372,130 A | 12/1994 | Stern et al. |
| 5,388,571 A | 2/1995 | Roberts et al. |
| 5,404,871 A | 4/1995 | Goodman et al. |
| 5,419,318 A | 5/1995 | Tayebi |
| 5,429,126 A | 7/1995 | Bracken |

(56) References Cited

U.S. PATENT DOCUMENTS

| | | |
|---|---|---|
| 5,429,683 A | 7/1995 | Le Mitouard |
| 5,431,158 A | 7/1995 | Tirotta |
| 5,438,981 A | 8/1995 | Starr et al. |
| 5,441,046 A | 8/1995 | Starr et al. |
| D362,061 S | 9/1995 | McGinnis et al. |
| 5,477,852 A | 12/1995 | Landis et al. |
| 5,479,920 A | 1/1996 | Piper et al. |
| 5,488,948 A | 2/1996 | Dubruille et al. |
| 5,492,116 A | 2/1996 | Scarberry et al. |
| 5,501,214 A | 3/1996 | Sabo |
| 5,509,404 A | 4/1996 | Lloyd et al. |
| 5,517,986 A | 5/1996 | Starr et al. |
| 5,538,000 A | 7/1996 | Rudolph |
| 5,540,223 A | 7/1996 | Starr et al. |
| 5,542,128 A | 8/1996 | Lomas |
| 5,546,936 A | 8/1996 | Virag et al. |
| RE35,339 E | 10/1996 | Rapoport |
| 5,560,354 A | 10/1996 | Berthon-Jones et al. |
| 5,570,682 A | 11/1996 | Johnson |
| 5,570,689 A | 11/1996 | Starr et al. |
| D377,089 S | 12/1996 | Starr et al. |
| 5,592,938 A | 1/1997 | Scarberry et al. |
| 5,608,647 A | 3/1997 | Rubsamen et al. |
| 5,642,730 A | 7/1997 | Baran |
| 5,647,355 A | 7/1997 | Starr et al. |
| 5,647,357 A | 7/1997 | Barnett et al. |
| 5,649,532 A | 7/1997 | Griffiths |
| 5,649,533 A | 7/1997 | Oren |
| 5,655,520 A | 8/1997 | Howe et al. |
| 5,655,527 A | 8/1997 | Scarberry et al. |
| 5,657,493 A | 8/1997 | Ferrero et al. |
| 5,657,752 A | 8/1997 | Landis et al. |
| 5,660,174 A | 8/1997 | Jacobelli |
| 5,662,101 A | 9/1997 | Ogden et al. |
| 5,666,946 A | 9/1997 | Langenback |
| 5,685,296 A | 11/1997 | Zdrojkowski et al. |
| 5,687,715 A | 11/1997 | Landis et al. |
| 5,715,814 A | 2/1998 | Ebers |
| 5,724,965 A | 3/1998 | Handke et al. |
| 5,746,201 A | 5/1998 | Kidd |
| 5,813,423 A | 9/1998 | Kirchgeorg |
| 5,832,918 A | 11/1998 | Pantino |
| 5,884,624 A | 3/1999 | Barnett et al. |
| 5,921,239 A | 7/1999 | McCall et al. |
| 6,082,360 A | 7/2000 | Rudolph et al. |
| 6,102,040 A | 8/2000 | Tayebi et al. |
| 6,112,746 A | 9/2000 | Kwok et al. |
| 6,119,693 A | 9/2000 | Kwok et al. |
| 6,357,441 B1 | 3/2002 | Kwok et al. |
| 6,412,487 B1 | 7/2002 | Gunaratnam et al. |
| 6,513,526 B2 | 2/2003 | Kwok et al. |
| 6,581,602 B2 | 6/2003 | Kwok et al. |
| 6,634,358 B2 | 10/2003 | Kwok et al. |
| 6,701,927 B2 | 3/2004 | Kwok et al. |
| 6,871,649 B2 | 3/2005 | Kwok et al. |
| 7,007,696 B2 | 3/2006 | Palkon et al. |
| 7,069,933 B2 | 7/2006 | Kwok et al. |
| 7,178,527 B2 | 2/2007 | Kwok et al. |
| 2004/0094159 A1 | 5/2004 | Kwok et al. |
| 2006/0201515 A1 | 9/2006 | Kwok et al. |

FOREIGN PATENT DOCUMENTS

| | | | |
|---|---|---|---|
| AU | 94/64816 B | | 12/1994 |
| AU | 95/16178 B | | 7/1995 |
| AU | 9459430 | | 2/1996 |
| AU | A 32914/95 | | 2/1996 |
| AU | A 41018/97 | | 4/1998 |
| AU | A 89312/98 | | 1/1999 |
| CA | 1039144 | | 9/1928 |
| DE | 459104 | | 4/1928 |
| DE | 701 690 | | 1/1941 |
| DE | 159396 | | 6/1981 |
| DE | 3015279 A1 | | 10/1981 |
| DE | 3345067 A1 | | 6/1984 |
| DE | 3537507 A1 | | 4/1987 |
| DE | 3539073 A1 | | 5/1987 |
| DE | 4004157 C1 | | 4/1991 |
| DE | 4343205 A1 | | 6/1995 |
| DE | 195 48 380 A1 | | 12/1995 |
| DE | 19548 380 A1 | | 12/1995 |
| DE | 197 35 359 | | 1/1998 |
| DE | 297 23 101 | | 7/1998 |
| DE | 298 10846 U1 | | 8/1998 |
| EP | 0 054 154 | | 10/1981 |
| EP | 0 252 052 | | 7/1987 |
| EP | 0 264 772 | | 10/1987 |
| EP | 303 090 B1 | | 7/1988 |
| EP | 0 386 605 A1 | | 2/1990 |
| EP | 0 462 701 A1 | | 5/1991 |
| EP | 0427474 A2 | | 5/1991 |
| EP | 0 303 090 B1 | | 4/1992 |
| EP | 0549 299 A2 | | 6/1993 |
| EP | 0 602 424 | | 11/1993 |
| EP | 0634186 A2 | | 6/1994 |
| EP | 0 608 684 A1 | | 4/1994 |
| EP | 0 697 225 | | 7/1995 |
| EP | 178 925 A2 | | 4/1996 |
| EP | 0 747 078 A2 | | 12/1996 |
| EP | 0 821 978 | | 2/1998 |
| FR | 801629 | | 8/1936 |
| FR | 858749 | | 12/1940 |
| FR | 2 574 657 A1 | | 6/1986 |
| FR | 2 658 725 A1 | | 8/1991 |
| FR | 2 749 176 | | 12/1997 |
| GB | 775911 | | 5/1957 |
| GB | 1395391 | | 5/1975 |
| GB | 1 467 828 | | 3/1977 |
| GB | 2005547 | | 4/1979 |
| GB | 2147506 A | | 5/1985 |
| GB | 2 164 569 A | | 3/1986 |
| GB | 2211098 A | | 6/1989 |
| GB | 2 267 648 A | | 12/1993 |
| GE | 2145335 A | | 3/1985 |
| IT | 326983 | | 6/1935 |
| JP | 44-16955 | | 7/1969 |
| JP | 54-90892 | | 7/1979 |
| JP | 09/216240 A | | 8/1997 |
| WO | WO 80/01044 | | 5/1980 |
| WO | WO 82/03548 | | 10/1982 |
| WO | WO 86/06969 | | 12/1986 |
| WO | WO 87/01950 | | 4/1987 |
| WO | WO 91/03277 | | 3/1991 |
| WO | WO 92/15353 | | 9/1992 |
| WO | WO 92/20395 | | 11/1992 |
| WO | WO 93/01854 | | 2/1993 |
| WO | WO 94/02190 | | 2/1994 |
| WO | WO 94/16759 | | 8/1994 |
| WO | 94/19055 | | 9/1994 |
| WO | WO 94/20051 | | 9/1994 |
| WO | WO 95/02428 | | 1/1995 |
| WO | WO 96/17643 | | 6/1996 |
| WO | WO 96/25983 | | 8/1996 |
| WO | WO 96/39206 | | 12/1996 |
| WO | WO 97/07847 | | 3/1997 |
| WO | WO 97/41911 | | 11/1997 |
| WO | WO 98/04310 | | 2/1998 |
| WO | WO 98/11930 | | 3/1998 |
| WO | WO 98/18514 | | 5/1998 |
| WO | WO 98/24499 | | 6/1998 |
| WO | WO 98/26829 | | 6/1998 |
| WO | WO 98/26830 | | 6/1998 |
| WO | WO 98/48878 | | 11/1998 |

OTHER PUBLICATIONS

Office Action for corresponding European Application No. 10184794.5, mailed Nov. 7, 2011.
Notice of Opposition for corresponding European Application No. 06115004.1, dated Feb. 9, 2012, 27 pages.
Decision on Appeal (and English translation) completed Mar. 25, 2008 for corresponding Japanese Application No. 2005-23339, 21 pages.

(56) References Cited

OTHER PUBLICATIONS

Respironics, Inc., "Nasal Mask and Accessories Guide", Dec. 23, 1991, 6 pages.
Respironics, Inc., "InterVENTions, A Ventilatory Care Newsletter", vol. 93, No. 1, Mar. 1993, 16 pages.
"Order" from *Respironics, Inc.* v. *ResCare Limited et al.* case, Civil Action No. 95-151, with Exhibits E and G related to information allegedly available before Jul. 26, 1995, 20 pages.
Respironics, Inc., Instructions for Use for the Comfort Flap Small Child Contour Nasal Mask Accessory, Jul. 19, 1993, 2 pages.
"Comfort Flap™ Improves the Seal on Reusable Contour Nasal Masks," InterVENTions, vol. 3, No. 1, Mar. 1993, 2 pages.
Mask 1 Photographs, Respironics Inc.. Reusable Full Mask (small) Part # 452033 Lot #951108.
Mask 2 Photographs, Puritan-Bennett, Adam Curcuit , Shell Part # 231700, Swivel Part # 616329-00, Pillows (medium) Part #616324. (no date, but admitted as prior art prior to critical date of application).
Mask 3, Photographs, DeVilbiss Healthcare Inc., DeVilbiss Seal-Ring and CPAP Mask Kit (medium), Part 73510-669. (no date, but admitted as prior art prior to critical date of application).
Mask 4 Photographs, Respironics Inc.. Monarch Mini Mask with Pressure Port, Part # 572004, Monarch Headgear, Part #572011. (no date, but admitted as prior art prior to critical date of application).
Mask 5 Photographs, Healthdyne Technologies, Nasal CPAP Mask (medium narrow), Part # 702510. (no date, but admitted as prior art prior to critical date of application).
Mask 6 Photographs, Healthdyne Technologies, Soft Series Nasal CPAP Mask, Part # 702020. (no date, but admitted as prior art prior to critical date of application).
Mask 7 Photographs, DeVilbiss Healthcare Inc., Small Mask and Seal Rings, Part # 73510-668. (no date, but admitted as prior art prior to critical date of application).
Mask 8 Photographs, Respironics Inc., Reusable Contour Mask (medium), Part # 302180. (no date, but admitted as prior art prior to critical date of application).
Mask 9 Photographs. Healthdyne Technologies, Healthdyne Large Headgear. (no date, but admitted as prior art prior to critical date of application).
Mask 10 Photographs, Respironics Inc., Soft Cap (medium), Part # 302142. (no date, but admitted as prior art prior to critical date of application).
Mask 11 Photographs, Weinmann: Hamburg, Nasalmaskensystem mit Schalldampfer (medium), Part # WN 23105. (no date, but admitted as prior art prior to critical date of application).
Mask 12 Photographs. Life Care (no date, but admitted as prior art prior to critical date of application).
Mask 13 Photographs, Healthdyne Technologies. (no date, but admitted as prior art prior to critical date of application).
Mask 14 Photograph, King System. (no date, but admitted as prior art prior to critical date of application).
Mask 15 Photographs, Respironics Inc.. Paediatric Mask. (no date, but admitted as prior art prior to critical date of application).
Mask 16 Photographs, Hans Rudolph Inc., Hans Rudolph Silicone Rubber Face Mask/8900. (no date, but admitted as prior art prior to critical date of application).
Japanese Office Action and Translation for Application No. 508323/1998, Mailed Jul. 1, 2003 (6 pages).
"ResMed Sullivan Mirage—The Mirage is Real—A Perfect Fit—First Time," product brochure © ResMed Limited 1997, 4 pages.
Mirage Spare Parts Brochure, 1997, 2 pages.

FULL-FACE MASK AND MASK CUSHION THEREFOR

CROSS REFERENCE TO RELATED APPLICATION

This is a continuation of U.S. application Ser. No. 11/432,436, filed May 12, 2006, now allowed, which is a continuation of U.S. application Ser. No. 10/704,754, filed Nov. 12, 2003, now U.S. Pat. No. 7,069,933, which is a continuation of U.S. application Ser. No. 10/166,282, filed Jun. 11, 2002, now U.S. Pat. No. 6,701,927, which is a continuation of U.S. application Ser. No. 09/316,227, filed May 21, 1999, now U.S. Pat. No. 6,513,526, which is a Continuation-in-Part of U.S. application Ser. No. 08/791,212, Jan. 31, 1997, now U.S. Pat. No. 6,112,746, which claims the benefit of Australian Patent Application No. PO 1265, filed Jul. 26, 1996, each incorporated herein by reference in its entirety.

FIELD OF THE INVENTION

The invention relates generally to a full-face (ie. nose and mouth) mask and to a cushion therefor, for example, for use in the treatment of respiratory conditions and in assisted respiration.

BACKGROUND OF THE INVENTION

Full-face masks are commonly used in the treatment of respiratory conditions and sleep disorders (e.g., obstructive sleep apnea) by delivering a flow of breathable gas for, or to assist, patient respiration. These masks typically receive a gas supply line which delivers gas into a chamber formed by walls of the mask. The walls usually are semi-rigid and have a face contacting portion including an aperture which is generally aligned with the wearer's nostrils and mouth. The face contacting portion can comprise a soft, resilient elastomeric material which may conform to various facial contours. The mask normally is secured to the wearer's head by straps. The straps are adjusted to pull the mask against the face with sufficient force to achieve a gas tight seal between the mask and the wearer's face. Gas is thus delivered to the mask and through the aperture to the wearer's nasal passages and throat.

Problems often arise with masks of the above configuration. For example, the mask may be dislodged, thereby breaking the seal between the mask and wearer. This may occur if the wearer rolls over when sleeping thereby creating a drag force on the gas supply line which is transmitted to the mask, breaking the seal. In the case of a mask being used for the administration of Continuous Positive Airway Pressure (CPAP) treatment for the condition obstructive sleep apnea, such a leak can result in the pressure supplied to the entrance of the wearer's airway being below the therapeutic value, and the treatment becoming ineffective.

Another problem is that the face contacting portion may apply excessive pressure to the wearer's face resulting in discomfort and possibly skin irritation. This can occur because the face contacting portion has to distort beyond its normal range of elasticity to conform to certain facial contours which requires the application of excessive forces. In some cases these excessive pressures and forces may cause the face to distort to conform with the face contacting portion to increase wearer discomfort, facial soreness and ulceration.

It is an object of the invention to overcome or at least substantially ameliorate one or more of the foregoing disadvantages.

SUMMARY OF THE INVENTION

In one broad form, the invention discloses a full-face mask cushion to sealingly connect a mask to a wearer's face, the cushion comprising:
a nasal bridge region, a cheek region and a chin region;
a first membrane comprising a substantially triangularly-shaped frame of resilient material having a first molded inwardly curved rim;
a second membrane of resilient material, said second membrane being thinner than said first membrane, said second membrane having a second molded inwardly curved rim, said second membrane curved rim spaced a first distance from said first membrane curved rim in said cheek region and said second membrane curved rim spaced a second distance from said first membrane curved rim in said nasal bridge region, said second distance greater than said first distance, said distances measured when the mask is not in use, a portion of said second membrane curved rim forming a face contacting seal.

Preferably, the rim and seal portion are shaped to generally match facial contours of the facial tissue around the sides and over the bridge of the nose and between the bottom lip and the chin.

In one particularly advantageous form, the membrane is substantially saddle-shaped. The membrane further has a centrally located aperture through which the wearer's nose and mouth pass to enter said cavity.

It is preferred that the cushion and membrane each include a co-located notch to accommodate the bridge of the nose of the wearer. Typically, the seal portion contacts at least the wearer's nose, and preferably, also the facial tissue around the sides and over the bridge of the nose and between the bottom lip and the chin.

The invention further discloses a full-face mask for connection to a wearer's face comprising:
a mask body for connection with a supply of breathable gas; and
a full-face cushion secured to said mask body, the body and cushion forming a nose and mouth-receiving cavity, said cushion including:
a nasal bridge region, a cheek region and a chin region;
a substantially triangularly-shaped first membrane of resilient material having a first molded inwardly curved rim to surround wearer's nose;
a second membrane also of resilient material, said second membrane being relatively more flexible than said first membrane, said second membrane having a second molded inwardly curved rim, said second molded rim being of the same general shape as said first molded rim and fixed to and extending away from said first membrane so as to have a second membrane inner surface spaced a first distance from an outer surface of said first molded rim in said cheek region and said second membrane inner surface spaced a second distance from said first membrane outer surface of said first molded rim in said nasal bridge region, said second distance greater than said first distance, said distances measured when the mask is not in use, a portion of said second molded rim forming a face contacting seal; and
wherein said seal portion is substantially coterminous with respect to said second molded rim and is resiliently deformable towards said first membrane in use of said mask.

The mask body can further include attachment points from which securing straps can be attached, and by which the mask can be secured to the wearer's head. The nasal mask can yet further comprise an arm depending from said body from which a further securing strap(s) can be attached.

The invention further discloses a CPAP treatment apparatus comprising:

a flow generator for the supply of gas at a pressure elevated above atmospheric pressure;

a gas delivery conduit coupled to said flow generator; and a full-face mask in turn coupled to said conduit to said nasal mask including:

a mask body for connection with a supply of breathable gas; and a full-face cushion secured to said mask body, the body and cushion forming a nose and mouth-receiving cavity, the cushion including:

a nasal bridge region, a cheek region and a chin region;

a substantially triangularly-shaped first membrane of resilient material having a first membrane having a molded inwardly curved rim;

a second membrane having a second molded inwardly curved rim also of resilient material, said second membrane being relatively more flexible than said first membrane, and being of the same general shape as said first molded inwardly curved rim and fixed to and extending away from said first membrane so as to have an inner surface spaced a first distance from said first molded rim in said cheek region and said second membrane inner surface spaced a second distance from said first molded rim, said second distance greater than said first distance, said distances measured when the mask is not in use, a portion of said second molded rim forming a face contacting seal; and wherein said seal portion is generally coterminous with respect to said second molded rim and is resiliently deformable towards said first membrane in use of said mask.

In one particularly preferred form, a supply of gas can be provided to said cavity, said supply of gas assisting, but not solely causing maintenance of a seal by said seal forming portion of said membrane to the face of the wearer in use of the cushion.

Advantageously, because the membrane and the rim are substantially shaped to the facial contour, and the membrane does not need to turn in on itself, as in the prior art, thus contacting the face without folds or creases. With the cushion/mask secured to the wearer's head, the headstraps need only to be tensioned to balance the force due to mask gas pressure that tends to lift the mask off the face. Such relatively lower mask-to-face pressure results in greater patient comfort, and a reduction in the likelihood of skin irritation.

BRIEF DESCRIPTION OF THE DRAWINGS

An embodiment of the invention will now be described with reference to the accompanying drawings, in which.

DESCRIPTION OF THE PREFERRED EMBODIMENTS

FIGS. 1 to 9 show a nasal cushion 30A and a nasal mask 60A embodying the present invention.

Figure 1:
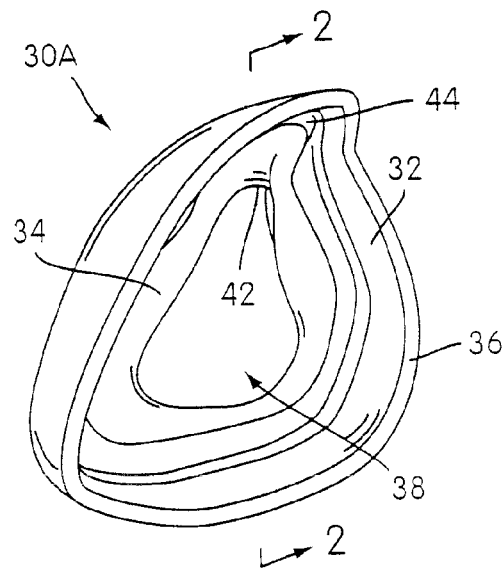
FIG. 1 is a rear perspective view of a nasal mask cushion embodying the present invention.
Figure 3:
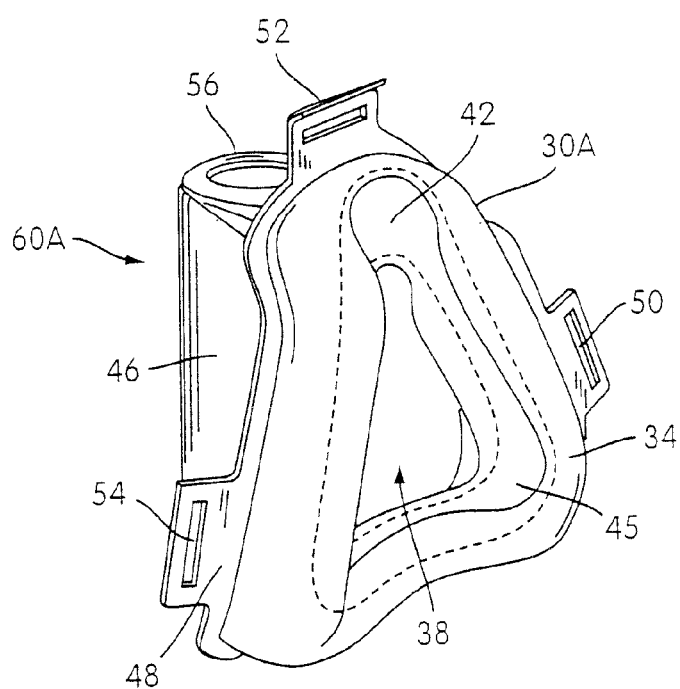
FIG. 3 is a perspective view of a nasal mask including the cushion of FIG. 1.

FIG. 1 is a perspective view of the nasal cushion 30A. FIG. 3 is a perspective view of the nasal cushion 30A attached to a mask body 46 to form the nasal mask 60A.

The nasal cushion 30A comprises a substantially triangularly shaped frame 32 from which extends a membrane 34. The frame 32 has a scalloped edge 36 by which the nasal cushion 30A is affixed to the mask body 46, as presently will be described.

The membrane 34 has an aperture 38 into which the wearer's nose is received in use of the nasal cushion 30A. The membrane 34 is spaced away from the rim 40 of the frame 32, and its outer surface 41 is of substantially the same shape as the rim 40. The outer surface 41 of the membrane 34 and the rim 40 of the frame 32 also can be described as generally saddle shaped. The shaping of the outer surface 41 of the membrane 34 and the rim 40 of the frame 32 also include respective notches 42,44 that receive the bridge of the wearer's nose in use of the nasal cushion 30A.

Figure 2:
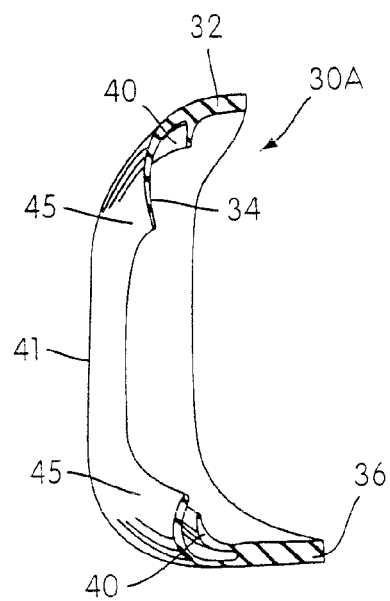
FIG. 2 is a cross-sectional view of the cushion shown in FIG. 1 along line 2-2.

As is best seen in FIG. 2, the frame 32 and the membrane 34 are integrally formed, typically in a one-shot molding process. The frame 32 and the membrane 34 are fabricated from a resilient material. One suitable such material is SILASTIC™ silicone elastomer manufactured by Dow Corning. The frame 32, in a preferred embodiment, has a typical thickness at its rim 40 of 1.5 mm. The membrane 34, in a preferred embodiment, has a typical thickness of 0.35 mm. In this way, the membrane 34 is relatively more flexible than the rim 40.

In use of the nasal cushion 30A, a wearer's nose will be inserted in the aperture 38 to engage a seal forming portion 45 (formed between the dashed lines) of the outer surface 41 to cause deformation of the membrane 34. Depending upon the securing force supplied to the membrane 34, it may deform to a point where it butts against the rim 40 of the frame 32. The frame 32 has a rigidity sufficient to withstand usual securing pressures in use of the nasal cushion 30A to tend to retain its shape and resist deformation. It thus acts as a supporting structure.

Referring now to FIG. 3, the nasal cushion 30A is shown attached to the mask body 46 by the edge 36 of the frame 32, adhered or otherwise secured to a flange 48 of the mask body 46. Only the outer surface 41 of the membrane 34 can be seen. The flange 48 includes two lower slots 50 and 54 from which a first tensioning strap 68 can be attached to secure the cushion 30 and the mask body 46 (in combination) to the head of a wearer.

The mask body 46 forms a cavity that can receive the nose of the wearer by the aperture 38. A port 56 is provided at the top of the mask body 46 by which breathable gas can be supplied to the chamber.

Figure 4:
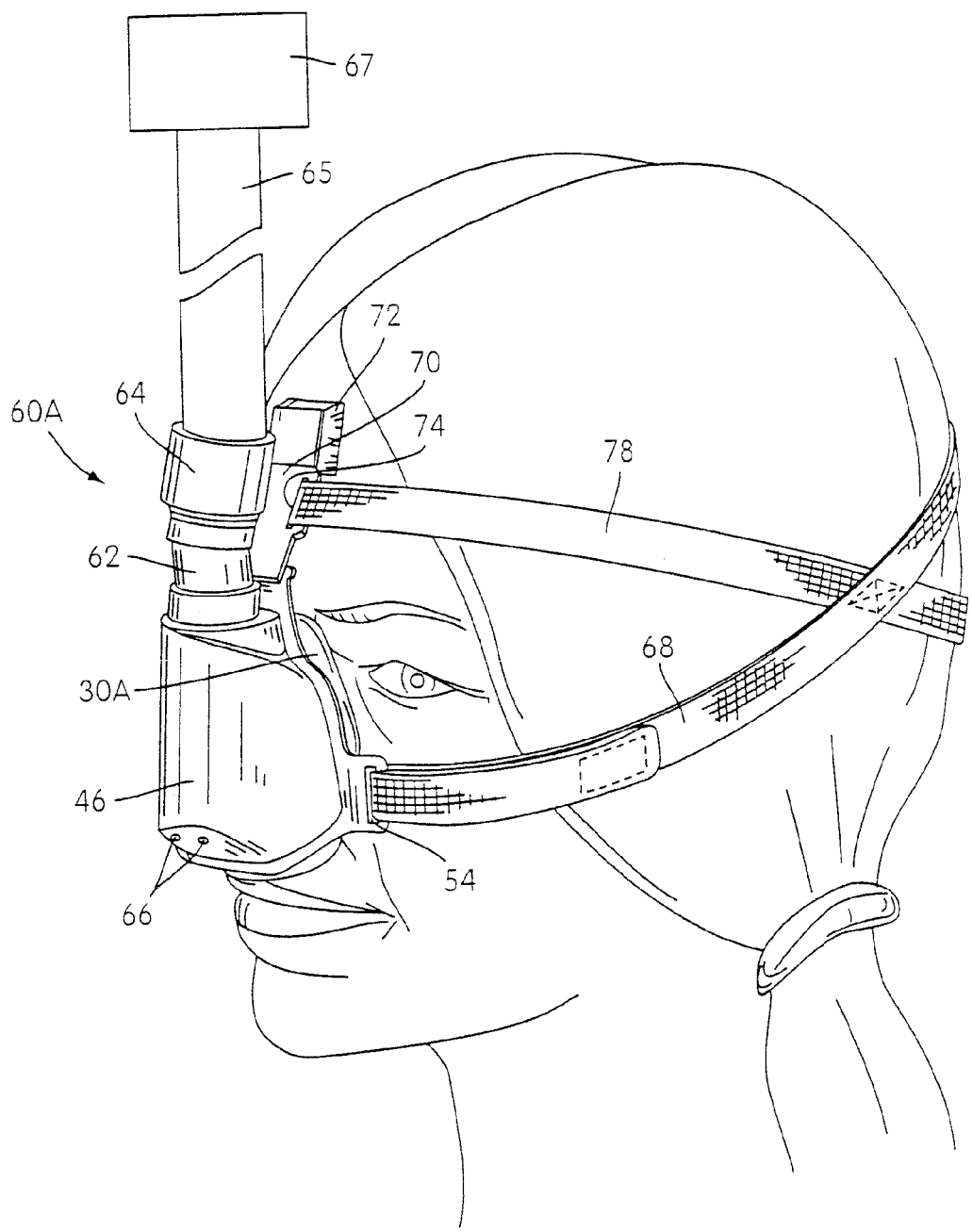
FIG. 4 is a perspective view of the nasal mask of FIG. 3 secured to a wearer's head.
Figure 5:
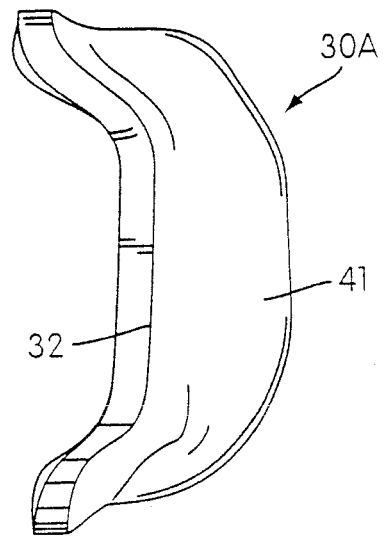
FIG. 5 is a side view of the mask cushion shown in FIG. 1.
Figure 6:
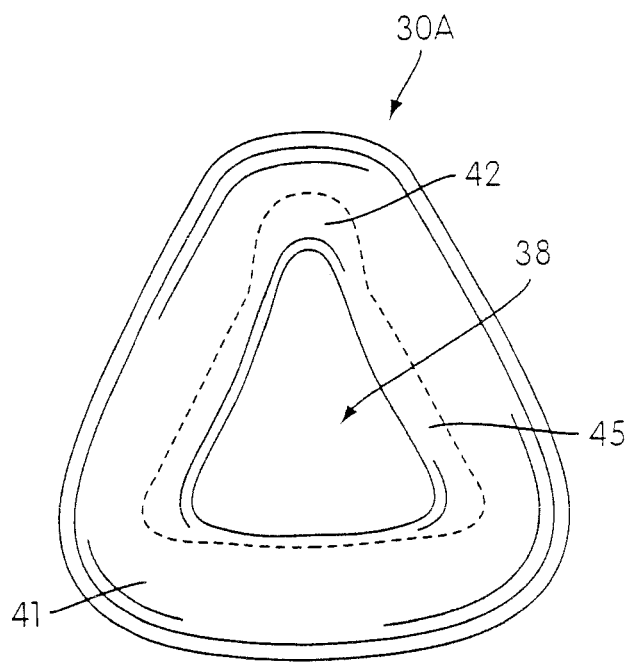
FIG. 6 is a front view of the mask cushion shown in FIG. 1.
Figure 7:
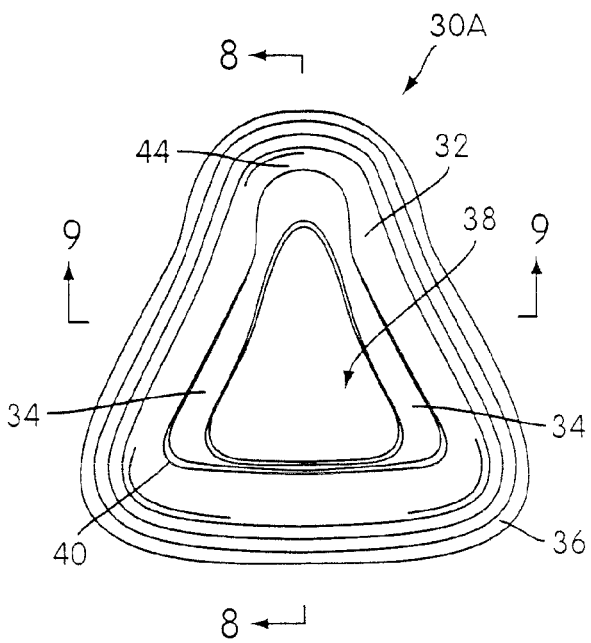
FIG. 7 is a rear view of the mask cushion shown in FIG. 1.
Figure 8:
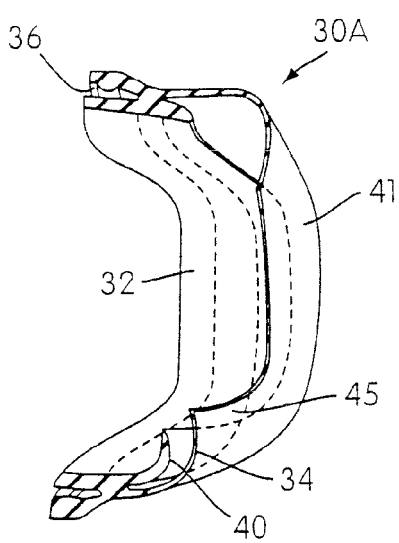
FIG. 8 is a cross sectional view of the mask shown in FIG. 1 along line 8-8 of FIG. 7.
Figure 9:
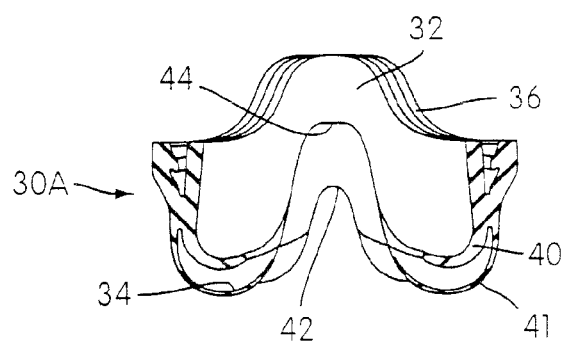
FIG. 9 is a cross sectional view of the mask shown in FIG. 1 along line 9-9 of FIG. 7.

Referring now to FIG. 4, a coupling tube 62 is shown above the nasal mask 60A. The coupling tube 62 is connected at one end with the inlet port 56, and at the other to a socket 64 into which can be received a gas delivery tube 65 for the supply of breathable gas to the chamber internal of the mask body 46 from a flow generator 67. The mask body 46 also has two vent openings 66 by which expired gas is exhausted. The first fastening strap 68 is fixed between the two lower slots 50,54. An upper slot 52 receives an arm 70, the top end of which has a resilient pad 72 to engage the forehead of the wearer. The arm 70 has two slots, only one slot 74 shown, along its side edges, by which a second fastening strap 78 is secured.

In fitting the nasal mask 60A, the wearer's nose is received through the aperture 38 into the chamber within the mask body 46. The seal forming portion 45 thus contacts both the surface of the wearer's nose and a portion of the wearer's face in the region between the base of the nose and the upper lip, and around the sides and over the bridge of the nose. The shape of the seal forming portion 45 is particularly suited to effectively seal the difficult region of the facial contour that is the crease between the sides of the nose and the face. Depending upon the tension applied by the first and second fastening straps 68,78, a seal is formed with the membrane 34 remaining spaced from the rim 40 of the cushion frame 32. While the provision of pressurised gas to the chamber of the mask body 46 assists in the maintenance of a seal between the membrane 34 and the wearer's nose and face, it is not essential in most cases, and an effective seal will be formed absent any such pressurised gas. When relative movement of the nasal mask 60A in relation to the wearer's head, the nose will be restrained by contacting the frame 32. Thus only limited relative motion between the nasal mask 60A and the wearer's nose and face occurs.

The membrane 34 closely imitates the facial contour, and because of its relatively lesser stiffness than the frame 32, can conform to particular facial structures with minimum force, and without a tendency to fold or crease.

If the fastening straps 68 and 78 are tensioned to excess, the membrane 34 deforms to abut the rim 40 of the cushion 30A, the frame 32 thus acting as an "end limit". In such a configuration, almost zero relative movement can occur between the nasal mask 60A and the wearer's head.

FIGS. 10 to 17 show a full-face cushion 30B and a full-face mask 60B embodying the present invention. Like reference numerals to those used in describing the "nasal" embodiment of FIGS. 1 to 9 shall be used to denote like features of the "full-face" embodiment of FIGS. 10 to 17.

Figure 10:
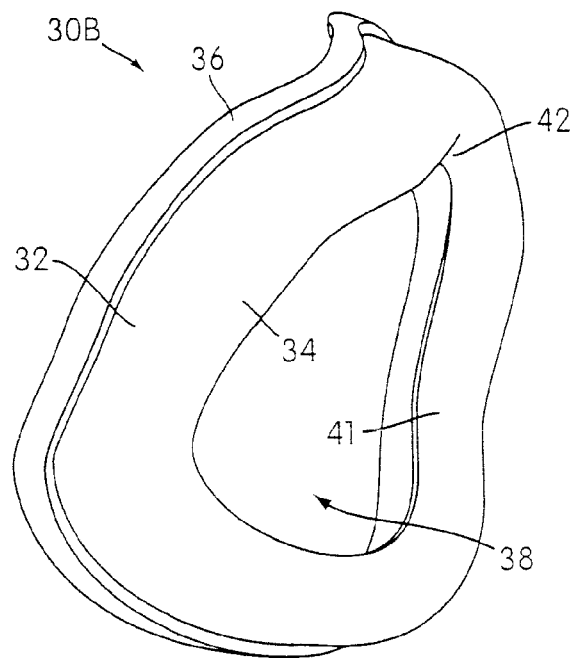
FIG. 10 is a front perspective view of a full-face mask cushion embodying the present invention.
Figure 11:
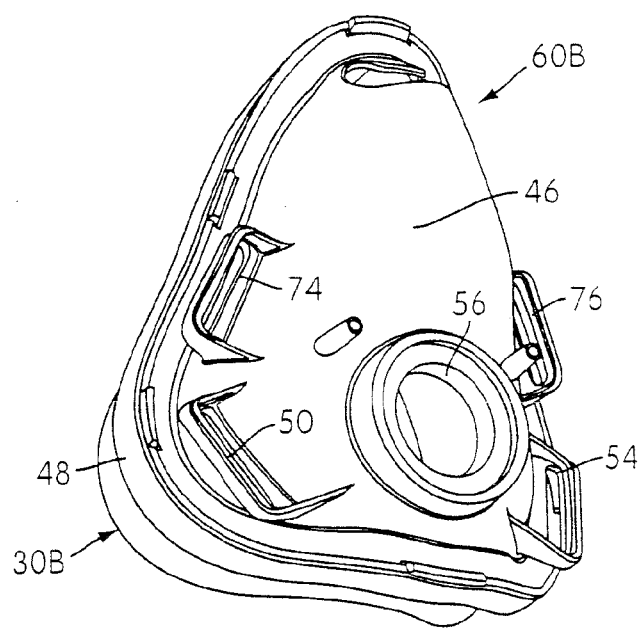
FIG. 11 is a perspective view of a full-face mask including the cushion of FIG. 10.
Figure 12:
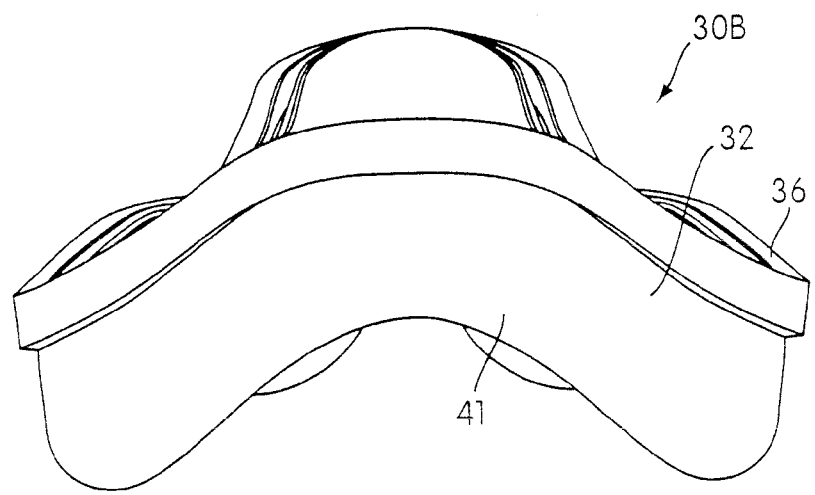
FIG. 12 is an underside view of the mask cushion shown in FIG. 10.
Figure 13:
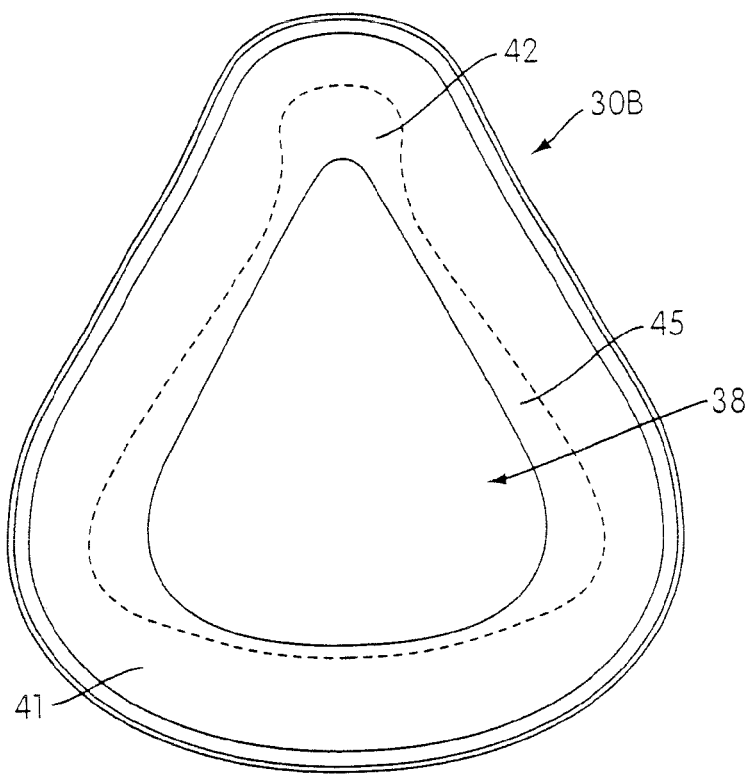
FIG. 13 is a front view of the mask cushion shown in FIG. 10.
Figure 14:
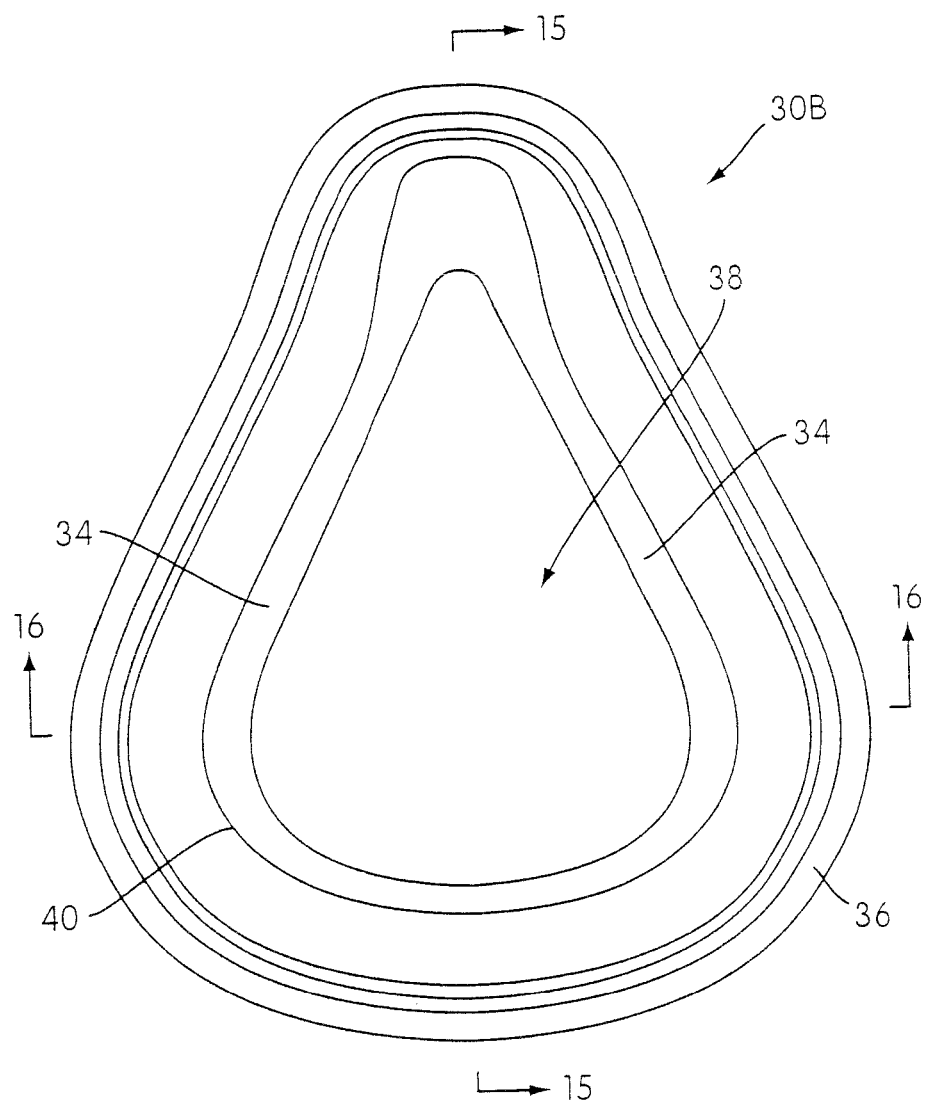
FIG. 14 is a rear view of the mask cushion shown in FIG. 10.
Figure 15:
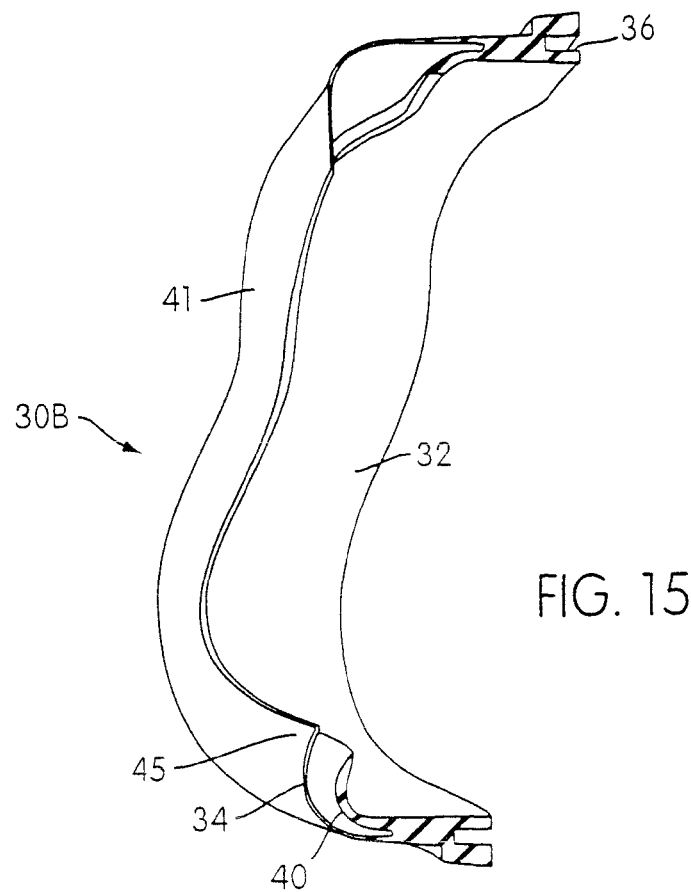
FIG. 15 is a cross sectional view of the mask cushion shown in FIG. 10 along line 15-15 of FIG. 14.

FIG. 10 is a perspective view of the full-face cushion 30B. FIG. 11 is a perspective view of the full-face cushion 30B attached to a mask body 46 to form the full-face mask 60B.

The full-face cushion 30B comprises a substantially triangularly shaped frame 32 from which extends a membrane 34. The frame 32 has a scalloped edge 36 by which the full-face cushion 30B is affixed to the mask body 46, as presently will be described.

The membrane 34 has an aperture 38 into which the wearer's nose and lips are received in use of the full-face cushion 30B. The membrane 34 is spaced away from the rim 40 of the frame 32, and its outer surface 41 is of substantially the same shape as the rim 40. The outer surface 41 of the membrane 34 and the rim 40 of the frame 32 also can be described as generally saddle shaped. The shaping of the outer surface 41 of the membrane 34 and the rim 40 of the frame 32 also include respective notches 42,44 that receive the bridge of the wearer's nose in use of the full-face cushion 30B.

Figure 16:
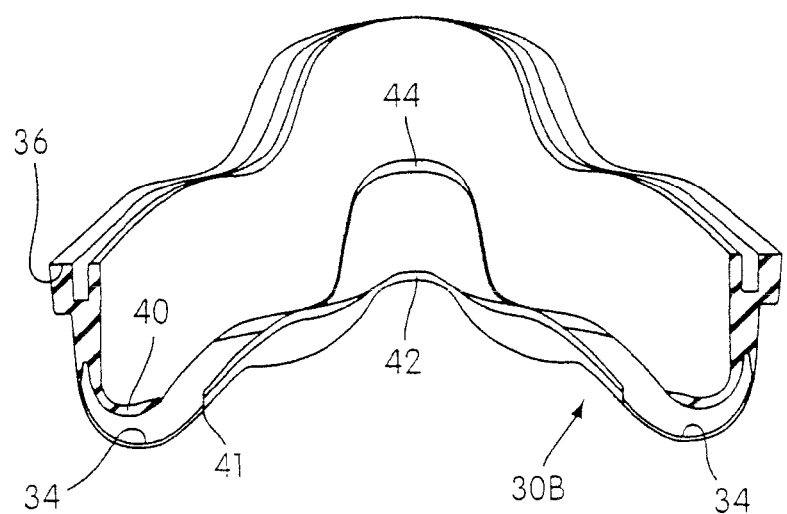
FIG. 16 is a cross sectional view of the mask cushion shown in FIG. 10 along line 16-16 of FIG. 14.

As is best seen in FIG. 16, the frame 32 and the membrane 34 are integrally formed, typically by in a one-shot molding process. The frame 32 and the membrane 34 are fabricated from a resilient material. One suitable such material is SILASTIC™ silicone elastomer manufactured by Dow Corning. The frame 32, in a preferred embodiment, has a typical thickness at its rim 40 of 1.5 mm. The membrane 34, in a preferred embodiment, has a typical thickness of 0.35 mm. In this way, the membrane 34 is relatively more flexible than the rim 40.

In use of the full-face cushion 30B, a wearer's nose and lips will be inserted in the aperture 38 to engage a seal forming portion 45 (formed inside the dashed line, see FIG. 13) of the outer surface 41 to cause deformation of the membrane 34. Depending upon the securing force supplied to the membrane 34, it may deform to a point where it butts against the rim 40 of the frame 32. The frame 32 has a rigidity sufficient to withstand usual securing pressures in use of the full-face cushion 30B to tend to retain its shape and resist deformation. It thus acts as a supporting structure.

Referring now to FIG. 11, the full-face cushion 30B is shown attached to the mask body 46 by the edge 36 of the frame 32, adhered or otherwise secured to a flange 48 of the mask body 46. Only the outer surface 41 of the membrane 34 can be seen. The mask body 46 includes two lower slots 50 and 54 and two upper slots 74 and 76 from which first and second tensioning straps 68 and 78 can respectively be attached to secure the cushion 30B and the mask body 46 (in combination) to the head of a wearer.

The mask body 46 forms a cavity that can receive the nose and lips of the wearer by the aperture 38. A port 56 is provided at the front of the mask body 46 by which breathable gas can be supplied to the chamber.

Figure 17:
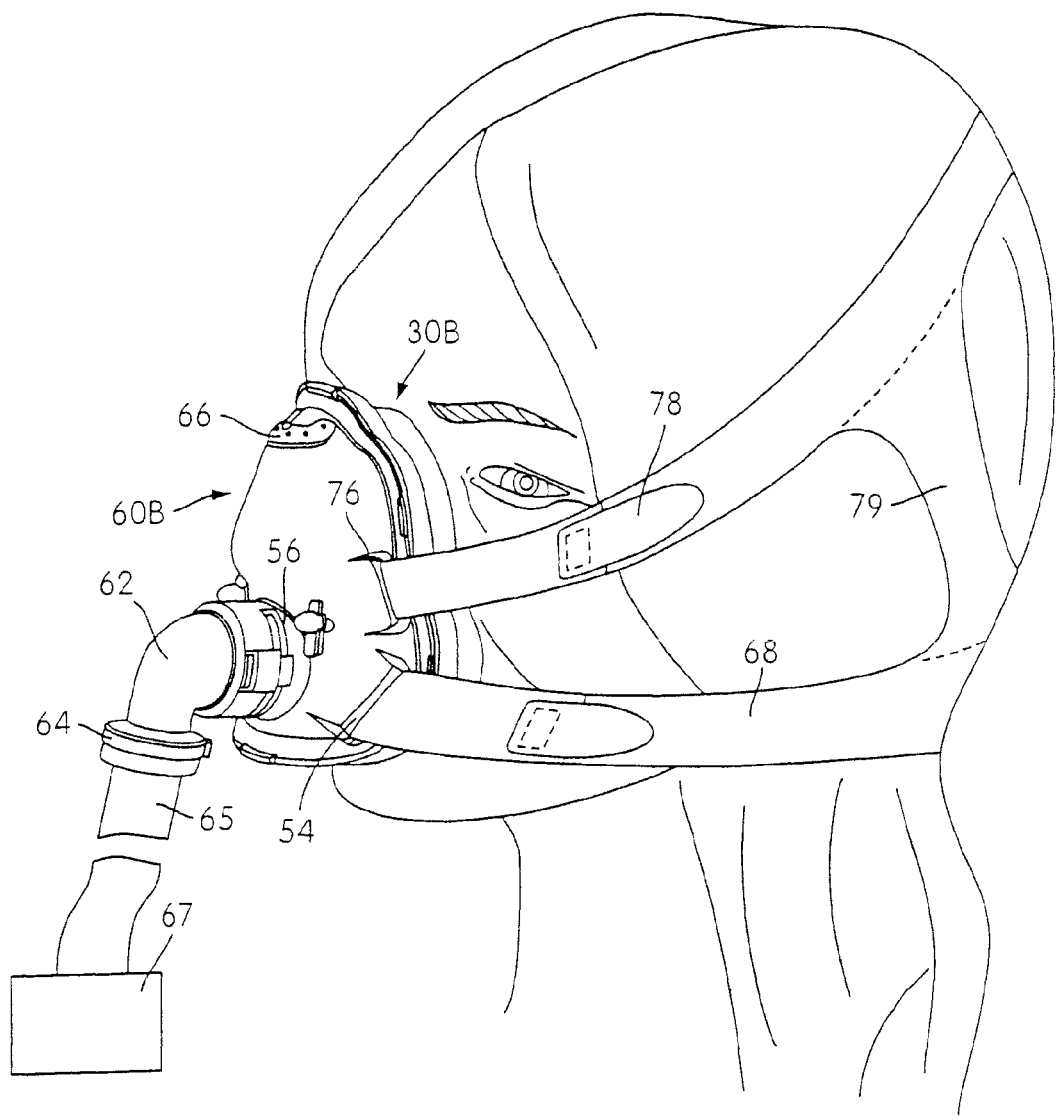
FIG. 17 is a perspective view of the mask shown in FIG. 11 secured to a wearer's face.

Referring now to FIG. 17, a coupling elbow 62 is shown connected at one end with the inlet port 56, and at the other to a socket 64 into which can be received a gas delivery tube 65 for the supply of breathable gas to the chamber internal of the mask body 46 from a flow generator 67. The mask body 46 also a vent opening 66 by which expired gas is exhausted. The first fastening strap 68 is fixed between to the lower two slots 50 and 54. The second fastening strap 78 is secured between the two upper slots 74 and 76. The first and second straps 68 and 78 are joined at each side by a bridging portion 79.

In fitting the full-face mask 60B, the wearer's nose and lips are received through the aperture 38 into the chamber within the mask body 46. The seal forming portion 45 thus contacts both the surface of the wearer's nose and a portion of the wearer's face in the region between the bottom lip and the chin, and around the sides and over the bridge of the nose. The shape of the seal forming portion 45 is particularly suited to effectively seal the difficult region of the facial contour that is the crease between the sides of the nose and the face. Depending upon the tension applied by the first and second fastening straps 68,78, a seal is formed with the membrane 34 remaining spaced from the rim 40 of the cushion frame 32. While the provision of pressurised gas to the chamber of the mask body 46 assists in the maintenance of a seal between the membrane 34 and the wearer's nose and face, it is not essential in most cases, and an effective seal will be formed absent any such pressurised gas. When relative movement of the full-face mask 60B in relation to the wearer's head, the nose will be restrained by contacting the frame 32. Thus only limited relative motion between the full-face mask 60B and the wearer's nose and face occurs.

The membrane 34 closely imitates the facial contour, and because of its relatively lesser stiffness than the frame 32, can conform to particular facial structures with minimum force, and without a tendency to fold or crease.

If the fastening straps 68 and 78 are tensioned to excess, the membrane 34 deforms to abut the rim 40 of the cushion 32, the frame 32 thus acting as an "end limit". In such a configuration, almost zero relative movement can occur between the full-face mask 60B and the wearer's head.

The nasal cushion 30A, the nasal mask 60A, the full-face cushion 30B and the full-face mask 60B have been described with reference to CPAP or assisted respiration treatment, however it is to be understood that the invention generally is applicable to any application where gas and/or atomised liquid is to be supplied to the entrance of the airways. Such applications include nebulisers, gas masks and anaesthetic machines.

We claim:

1. A mask assembly for delivery of a supply of gas to an entrance to the airways of a patient, said patient having a nasal bridge region, a cheek region and a chin region, said mask assembly comprising:
   a headstrap system to secure the mask assembly relative to the patient's head; and
   a cushion adapted to confront the face of the patient, said cushion comprising first and second membranes of integrally formed elastomeric material, each of said first and second membranes having an aperture adapted to receive the patient's nose and mouth,
      said second membrane defines a seal-forming portion on an outer surface thereof, said seal-forming portion being constructed and arranged to be positioned adjacent the nasal bridge region of the patient, along sides of the patient's nose, and below lips or on the chin of the patient to effect a seal,
   the seal forming portion is structured such that it is not required to turn in on itself to conform with the patient's face,
   said first membrane provides a supporting structure for the second membrane,
   said second membrane covering said first membrane,
   wherein the second membrane is substantially unsupported by the first membrane where the cushion is adapted to seal with the nasal bridge region in use.

2. The mask assembly of claim 1, wherein, in a portion of the cushion adapted to contact the chin region, each of the first and second membranes extend a chin region distance toward their respective aperture, the chin region distances of the first and second membranes being generally equal.

3. The mask assembly of claim 2, wherein, in a portion of the cushion adapted to contact the cheek region, the second membrane extends a cheek region distance towards the aperture of the second membrane, the cheek region distance being greater than the chin region distance of the second membrane.

4. The mask assembly of claim 3, wherein, in the nasal bridge region, the second membrane extends a nasal bridge region distance that is greater than the chin region distance of the second membrane.

5. The mask assembly of claim 4, wherein in the nasal bridge region, the second membrane extends towards the aperture of the second membrane to a degree relative to the first membrane that is greater than that of the second membrane relative to the first membrane in the cheek region.

6. The mask assembly of claim 1, wherein, in the nasal bridge region, the shape between the first and second membranes is different from one another such that the nasal bridge is able to be inserted into a space where there is substantially no first membrane, with the second membrane stretching across a gap in the first membrane.

7. The mask assembly of claim 1, further comprising a notch in both the first and second membranes to receive the bridge of the wearer's nose.

8. The mask assembly of claim 1, wherein the first membrane has a thickness of about 1.5 mm and the second membrane has a thickness of about 0.35 mm.

9. The mask assembly of claim 1, wherein the first membrane extends a first distance towards the aperture of the first membrane in the nasal bridge region, and a second distance towards the aperture of the first membrane in the chin region, wherein said first distance is less than said second distance.

* * * * *